US011376253B2

United States Patent
Segawa et al.

(10) Patent No.: US 11,376,253 B2
(45) Date of Patent: Jul. 5, 2022

(54) AGENT FOR TREATING NOCTURNAL POLLAKIURIA

(71) Applicant: KYORIN PHARMACEUTICAL CO., LTD., Tokyo (JP)

(72) Inventors: Katsuya Segawa, Tokyo (JP); Takafumi Kurose, Tokyo (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/768,972

(22) PCT Filed: Dec. 20, 2018

(86) PCT No.: PCT/JP2018/047038
§ 371 (c)(1),
(2) Date: Jun. 2, 2020

(87) PCT Pub. No.: WO2019/124507
PCT Pub. Date: Jun. 27, 2019

(65) Prior Publication Data
US 2021/0000831 A1 Jan. 7, 2021

(30) Foreign Application Priority Data
Dec. 21, 2017 (JP) .............................. JP2017-244910
Nov. 12, 2018 (JP) .............................. JP2018-212256

(51) Int. Cl.
*A61K 31/519* (2006.01)
*A61P 13/10* (2006.01)
*A61K 9/00* (2006.01)

(52) U.S. Cl.
CPC ............ *A61K 31/519* (2013.01); *A61P 13/10* (2018.01); *A61K 9/0053* (2013.01)

(58) Field of Classification Search
CPC ...... A61K 31/519; A61K 9/0053; A61P 13/10; A61P 43/00
See application file for complete search history.

(56) References Cited

U.S. PATENT DOCUMENTS

2009/0253705 A1   10/2009   Berger et al.

FOREIGN PATENT DOCUMENTS

| JP | 2011-510023 | 3/2011 | | |
|---|---|---|---|---|
| WO | 2009/124167 | 10/2009 | | |
| WO | WO-2011043942 A1 | * | 4/2011 | ......... A61K 31/4025 |
| WO | WO-2017210696 A1 | * | 12/2017 | ........... A61K 31/137 |
| WO | WO-2018224990 A1 | * | 12/2018 | ......... A61K 31/7048 |

OTHER PUBLICATIONS

Kujubu, Geriatric Nephrology Curriculum, publ. 2009, American Soc. Nephrology, chapter 19, pp. 1-4 (Year: 2009).*
Fitzgerald et. al., Int. Urogynecol. J. Pelvic Floor Dysfunct., publ. 2008, vol. 19(11), pp. 1545-1550 (1-13) (Year: 2008).*
Yoshida et. al., Int. J. Urology, vol. 26, pp. 369-375, publ. Dec. 17, 2018 (Year: 2018).*
Translation of International Preliminary Report on Patentability dated Jul. 2, 2020 in International (PCT) Application No. PCT/JP2018/047038.
International Search Report (ISR) dated Feb. 5, 2019 in International (PCT) Application No. PCT/JP2018/047038.
Victor W. Nitti et al., "Results of a Randomized Phase III Trial of Mirabegron in Patients with Overactive Bladder", The Journal of Urology, vol. 189, issue 4, pp. 1388-1395, Apr. 1, 2013, cited in the specification & CA.
Nihon Hainyou Kinou Gakkai Yakanhinnyou Sinryou Guideline Sakusei Iinkai (in Japanese) (Preparation Committee on Practice Guideline for Nocturnal Pollakiuria of The Japanese Continence Society), Yakanhinnyou Sinryou Guideline Dai 1 Pan (in Japanese) (Practice Guideline for Nocturnal Pollakiuria, the first edition), 2009, cited in the specification.
Mark Weatherall, "The Risk of Hyponatremia in Older Adults Using Desmopressin for Nocturia: A Systematic Review and Meta-Analysis", Neurourology and Urodynamics, vol. 23, pp. 302-305, 2004, Package inserts of Minirinmelt OD tablet 60 μg, Minirinmelt OD tablet 120 μg, and Minirinmelt OD tablet 240 μg, revised in Mar. 2017 (the fourth edition), cited in the specification.
Package inserts of Betanis (R) 25 mg and Betanis (R) tablet 50 mg, revised in Mar. 2016 (the ninth edition), cited in the specification.
Interview forms of Betanis (R) tablet 25 mg and Betanis tablet (R) 50 mg, revised in 2016, cited in the specification.
Hann-Chorng Kuo et al., "Results of a Randomized, Double-Bind, Parallel-Group, Placebo- And Active-Controlled, Multicenter Study of Mirabegron, a β3 -adrenoceptor Agonist, in Patients with Overactive Bladder in Asia", Neurourology and Urodynamics, vol. 34, No. 7, pp. 685-692, 2015, cited in the specification.
Osamu Yamaguchi et al., "Phase III, randomised, double-blind, placebo-controlled study of the $β_3$-adrenoceptoer agonist mirabegron, 50 mg once daily, in Japanese patients with overactive bladder", BJU International, vol. 113, No. 6, pp. 951-960, 2014, cited in the specification.
Christopher R. Chapple et al., "Mirabegron 50 mg once-daily for the treatment of symptoms of overactive bladder: An overview of efficacy and tolerability over 12 weeks and 1 year", International Journal of Urology, vol. 21, No. 10, pp. 960-967, 2014, cited in the specification.
Christopher R. Chapple et al., "A Proof-of-Concept Study: Mirabegron, A New Therapy for Overactive Bladder", Neurourology and Urodynamics, vol. 32, No. 8, pp. 1116-1122, 2013, cited in the specification.
Emmanuel Chartier-Kastler et al., "The Measurement of Nocturia and Its Impact on Quality of Sleep and Quality of Life in LUTS/BPH", Emopean Urology Supplements, vol. 5, pp. 3-11, 2006, cited in the specification.

(Continued)

Primary Examiner — Sarah Pihonak
(74) Attorney, Agent, or Firm — Wenderoth, Lind & Ponack, L.L.P.

(57) ABSTRACT

[Problem] To provide a novel therapeutic agent for nocturnal pollakiuria.
[Solution] A therapeutic agent for nocturnal pollakiuria which contains, as an active ingredient, (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide.

4 Claims, 2 Drawing Sheets

(56) References Cited

OTHER PUBLICATIONS

Derk-Jan Dijk et al., "Sleep Extension in Humans: Sleep Stages, EEG Power Spectra and Body Temperature", Sleep, vol. 14, pp. 294-306, 1991, cited in the specification.
Extended European Search Report dated Sep. 15, 2021 in corresponding European Patent Application No. 18890939.4.
Anonymous, "A Study of the Efficacy and Safety of Vibegron (MK-4618) in Participants With Overactive Bladder (OAB) (MK-4618-008)", Clinical Trials.gov (NCT01314872), pp. 1-31, Jun. 17, 2016.

\* cited by examiner

AGENT FOR TREATING NOCTURNAL POLLAKIURIA

TECHNICAL FIELD

The present invention relates to an agent for treating nocturnal pollakiuria.

BACKGROUND ART

Nocturnal pollakiuria is a complaint that one has to wake up one or more times for urinating at night, and is one of the symptoms (urinary urgency, pollakiuria, nocturnal pollakiuria, and urge urinary incontinence) resulting from overactive bladder (OAB). Nocturnal pollakiuria causes nocturnal awakening and is closely associated with sleep disorders, thereby reducing QOL remarkably (Non Patent Literature 1).

Desmopressin, which is an agonist of vasopressin V2 receptor, has been known so far as a therapeutic drug for nocturnal pollakiuria: however, desmopressin has a risk of serious adverse reactions such as water intoxication (hyponatremia) and can be administered only to a restricted group of patients (Non Patent Literature 2).

Furthermore, mirabegron, which is an agonist of β3 adrenergic receptor, can be administered only to a restricted group of patients. For example, administration of mirabegron to patients of reproductive age needs to be avoided (Non Patent Literature 3). There has been no report on mirabegron indicating a significant difference in therapeutic effect on nocturnal pollakiuria in Japanese subjects as compared with a placebo (Non Patent Literatures 4 to 9).

Vibegron (a compound represented by general formula (1) or expressed as (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide) is known as a compound that is an agonist of β3 adrenergic receptor similarly to mirabegron (Patent Literature 1).

[Formula 1]

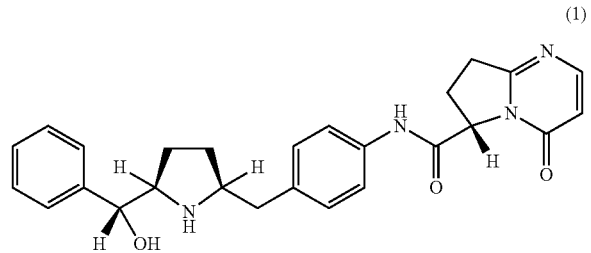

(1)

CITATION LIST

Patent Literature

Patent Literature 1: International Publication No. WO 2009124167

Non Patent Literature

Non Patent Literature 1: Nihon Hainyou Kinou Gakkai Yakanhinnyou Sinryou Guideline Sakusei Iinkai (in Japanese) (Preparation Committee on Practice Guideline for Nocturnal Pollakiuria of The Japanese Continence Society) (2009), Yakanhinnyou Sinryou Guideline Dai 1 Pan (in Japanese) (Practice Guideline for Nocturnal Pollakiuria, the first edition).

Non Patent Literature 2: Neurourol Urodyn 2004; 23: 302-305, Package inserts of Minirinmelt OD tablet 60 μg, Minirinmelt OD tablet 120 μg, and Minirinmelt OD tablet 240 μg, revised in March 2017 (the fourth edition).

Non Patent Literature 3: Package inserts of Betanis® 25 mg and Betanis® tablet 50 mg, revised in March 2016 (the ninth edition).

Non Patent Literature 4: Interview forms of Betanis® tablet 25 mg and Betanis Tablet® 50 mg, revised in 2016.

Non Patent Literature 5: Neurourology and Urodynamics (2015), 34 (7), 685-692.

Non Patent Literature 6: BJU International (2014), 113 (6), 951-960.

Non Patent Literature 7: International Journal of Urology (2014), 21 (10), 960-967.

Non Patent Literature 8: Neurourology and Urodynamics (2013), 32 (8), 1116-1122.

Non Patent Literature 9: Journal of Urology (New York, N.Y., United States) (2013), 189 (4), 1388-1395.

SUMMARY OF INVENTION

Technical Problem

It is an object of the present invention to provide a novel agent for treating nocturnal pollakiuria.

Solution to Problem

The present inventors have conducted extensive studies of a more effective and safe agent for treating nocturnal pollakiuria. Consequently, the present inventors have found that a compound represented by general formula (1), namely, (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is highly effective as the agent for treating nocturnal pollakiuria and completed the present invention.

The present invention includes the following embodiments.

[1] An agent for treating nocturnal pollakiuria comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient.

[2] The agent according to [1], wherein the agent for treating nocturnal pollakiuria is administered to a subject belonging to a group of patients whose average value of the frequency of urination at night is 1.0 or more and 1.8 or less.

[3] The agent according to [1] or [2], wherein the agent is administered orally once daily at a daily dosage of 50 mg or more and 100 mg or less of the active ingredient.

[4] An agent for nocturnal pollakiuria comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient, wherein the agent is administered to an Asian.

[5] An agent for treating nocturnal pollakiuria comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient, wherein the agent is administered to a Japanese.

[6] An agent for treating sleep disorder associated with nocturnal pollakiuria comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient.

[7] The agent according to any one of [1] to [6], wherein the nocturnal pollakiuria is nocturnal pollakiuria without nocturnal polyuria.

[8] A method for treating nocturnal pollakiuria, comprising administering to a subject in need thereof (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide in an effective amount to treat nocturnal pollakiuria.

[9] The method according to [8], wherein (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered to a subject belonging to a group of patients whose average value of the frequency of urination at night is 1.0 or more and 1.8 or less.

[10] The method according to [8] or [9], wherein (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered orally once daily at a daily dosage of 50 mg or more and 100 mg or less.

[11] Use of (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide in the manufacture of a medicament for treating nocturnal pollakiuria.

[12] The use according to [11], wherein (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered to a subject belonging to a group of patients whose average value of the frequency of urination at night is 1.0 or more and 1.8 or less.

[13] The use according to [11] or [12], wherein (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered orally once daily at a daily dosage of 50 mg or more and 100 mg or less.

[14] A compound (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide for treating nocturnal pollakiuria.

[15] The compound for treating nocturnal pollakiuria according to [14], wherein the compound is administered to a subject belonging to a group of patients whose average value of the frequency of urination at night is 1.0 or more and 1.8 or less.

[16] The compound for treating nocturnal pollakiuria according to [14] or [15], wherein the compound is administered orally once daily at a daily dosage of 50 mg or more and 100 mg or less.

Advantageous Effects of Invention

The agent of the present invention has an excellent effect of reducing the frequency of urination at night, and thus, can be used advantageously as the agent for treating nocturnal pollakiuria.

DESCRIPTION OF EMBODIMENTS

Figure 1:
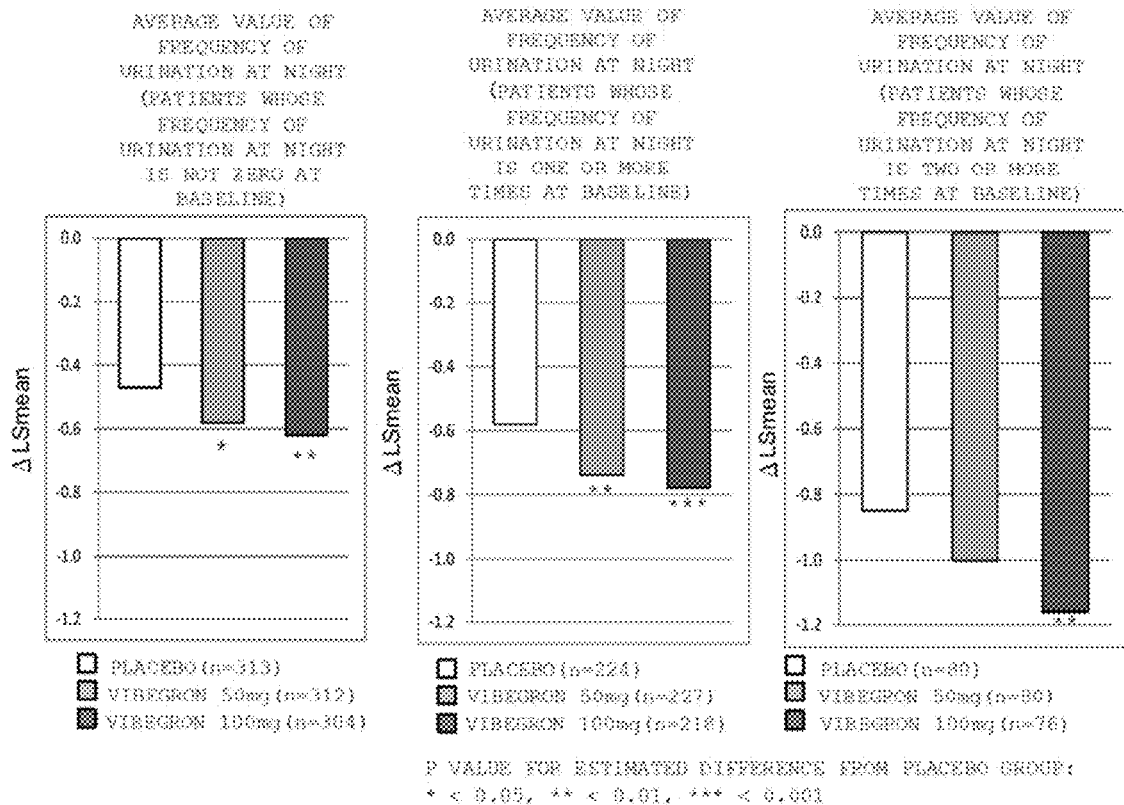
FIG. 1 is a graph showing the least squares mean (ΔLSmean) of the amount of change from baseline in the frequency of urination at night after 12 weeks of administration.

Hereinafter, an embodiment of the present invention will be described in detail, but the present invention is not limited to this embodiment.

As used herein, "nocturnal pollakiuria" refers to a condition in which one has to wake up one or more times for urinating at night. "At night" refers to the period of time between when one goes to bed to sleep and when one wakes up and gets out of bed.

Parameters for expressing the level of nocturnal pollakiuria include "frequency of nocturnal pollakiuria" and "frequency of urination at night." The former represents the frequency of urination that was recorded during sleep at night, provided that one is sleeping before and after urination. Therefore, the number of times when one was unable to sleep after getting into bed and went to the toilet is not counted in the "frequency of nocturnal pollakiuria." On the other hand, the latter represents the frequency of urination between the timepoint when one went to bed for sleeping and the timepoint when one got up (got out of bed) for rising. Therefore, urination that was done after going to bed and before falling asleep and urination that was done after awaking and urinating early morning and before falling asleep again are counted in the frequency of urination at night. Herein, the frequency of urination at night is used to evaluate the level of nocturnal pollakiuria.

As used herein, "treatment" refers to alleviating or reducing at least one of the diseases or conditions of a subject.

The agent for treating nocturnal pollakiuria of the present invention relaxes the bladder, thereby enhancing urine storage function thereof. Therefore, the agent is preferably used for "nocturnal pollakiuria associated with a reduced capacity of the bladder", and is more preferably used for "nocturnal pollakiuria associated with overactive bladder."

The agent for treating nocturnal pollakiuria of the present invention is preferably administered to a human. In this specification, examples of the human include an Asian, a Caucasian, a colored person, an African American, and a Hispanic. The agent for treating nocturnal pollakiuria of the present invention is preferably administered to an Asian, and more preferably administered to a Japanese (A significant difference compared with a placebo was seen when the agent for treating nocturnal pollakiuria of the present invention was administered to a Japanese).

An "Asian" as used herein is synonymous with the term generally used in clinical studies and examples thereof include a Taiwanese, a Korean, a Chinese, and a Japanese.

A "Japanese" as used herein is synonymous with the term generally used in clinical studies, and has a narrower meaning compared with a generally used definition of a Japanese, which is based on nationality. More specifically, the "Japanese" as used herein refers to a person whose parents and grandparents are not a foreigner. Therefore, a person whose at least one of the father and the mother is a foreigner and a person whose at least one of the grandfathers and the grandmothers is a foreigner are excluded from the definition of "Japanese" used herein.

An "average value of the frequency of urination at night" as used herein refers to an average value of the frequency of urination between when one goes to bed to sleep and when one wakes up and gets out of bed. This average value is zero or more and less than one in a population of healthy subjects and is 1.0 or more in a population of patients with nocturnal pollakiuria. A group of patients with a higher numerical value is a group of patients with severer nocturnal pollakiuria. The agent for treating nocturnal pollakiuria of the present invention is more effective for a group of patients with mild to severe nocturnal pollakiuria, and preferably is administered to a subject belonging to a group of patients whose average value of the frequency of urination at night is 1.0 or more. For example, the agent is administered to a subject belonging to a group of patients whose average value of interest is more preferably 1.0 or more and 1.8 or less, even more preferably 1.2 or more and 1.8 or less, and particularly preferably 1.3 or more and 1.7 or less. In this context, the "average value of the frequency of urination at night" may be referred to as "average frequency of urination at night."

A "single voided volume at night" as used herein refers to a voided volume per urination at night.

"Time to first awakening" as used herein may be referred to as HUS (hours of undisturbed sleep) and refers to time from falling asleep to first awakening to urinate.

A "first voided volume at night" as used herein refers to a voided volume of the first urination at night.

A pharmaceutical composition comprising a pharmaceutically acceptable additive may be used as an agent for treating nocturnal pollakiuria comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient. Examples of the pharmaceutically acceptable additive include an excipient, a lubricant, a binder, a disintegrant, a stabilizer, a flavoring agent, and a diluent. These additives are not particularly limited as long as they can be used for manufacturing a pharmaceutical preparation, and for example, those listed in "Japanese Pharmaceutical Excipients Directory (International Pharmaceutical Excipients Council Japan, Yakuji Nippo, Limited (2016)) can be used as appropriate.

"Comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient" means that any substance can be used as long as the substance comprises (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide as an active ingredient. Thus, a pharmaceutically acceptable salt or a cocrystal thereof may be administered when administered to a subject.

The pharmaceutically acceptable salt of (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide means a salt with a pharmaceutically acceptable nontoxic acid (for example, an organic acid or an inorganic acid). Examples of the salt with a pharmaceutically acceptable nontoxic acid include an acid addition salt with a mineral acid such as hydrochloric acid, hydrobromic acid, sulfuric acid, and nitric acid and an acid addition salt with an organic acid such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

The pharmaceutically acceptable cocrystal of (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide means a cocrystal with a generally used cocrystal former. Examples of the generally used cocrystal former include those described in WO 2004078163.

Furthermore, (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide or a pharmaceutically acceptable salt thereof may exist as a hydrate.

Furthermore, (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide or a pharmaceutically acceptable salt thereof may exist in a plurality of crystal forms or non-crystal (amorphous) forms, and any of the crystal forms or non-crystal forms may be administered.

The agent of this embodiment can be administered to a subject such as a human by applying a form and an administration route that are conventionally well known in the pharmaceutical field. For example, the agent can be administered orally or parenterally as a formulation such as a powder, a tablet, a capsule, a fine granule, a granule, a syrup, an injection, an ophthalmic solution, an aqueous nasal drop, an aqueous ear drop, and an inhalation solution. Specifically, the agent of this embodiment can be produced for example in the dosage form as described above by mixing the active ingredient with a carrier, an excipient, a binder, a diluent, and the like that are physiologically acceptable.

In order that the agent of this embodiment can exert a medicinal effect and reduce adverse reactions, a daily dosage of (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is preferably 10 mg or more and 250 mg or less, for example in the case of oral administration. The daily dosage is more preferably 30 mg or more and 160 mg or less, even more preferably 40 mg or more and 150 mg or less, and still more preferably 50 mg or more and 100 mg or less. More specific examples of the daily dosage include 50 mg, 62.5 mg, 75 mg, 87.5 mg, and 100 mg, among which 50 mg is more preferable. The daily dosage may be increased up to 100 mg depending on the symptoms. Although the daily dosage may be administered as a single dose or as two to three divided doses, a once daily dosing is preferable.

When the pharmaceutically acceptable salt, cocrystal, or hydrate of (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is used, the above daily dosage is an amount in terms of free form thereof.

The "free form" refers to (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide not in any form of a salt, a cocrystal, or a hydrate, and is a compound whose molecular formula is $C_{26}H_{28}N_4O_3$ and molecular weight is 444.53.

This embodiment can provide an agent for treating nocturnal pollakiuria that is excellent in efficacy and safety.

Furthermore, one aspect of the present invention relates to a method for treating nocturnal pollakiuria, comprising administering to a subject in need thereof (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide in an effective amount to treat nocturnal pollakiuria.

Furthermore, one embodiment of the present invention relates to a use of (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide in the manufacture of a medicament for treating nocturnal pollakiuria.

Furthermore, one aspect of the present invention relates to (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide for treating nocturnal pollakiuria.

Again, in these aspects, any substance can be used as long as (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is used as the active ingredient. Thus, a pharmaceutically acceptable salt or a cocrystal thereof may be administered when administered to a subject.

EXAMPLES

The present invention will be described in more detail with reference to the following Examples, but these Examples are not intended to limit the scope of the present invention.

Vibegron (compound represented by general formula (1) or (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide) was produced according to the method disclosed in WO 2009124167. A formulation to be administered orally to patients was produced by using an additive and a production method that were generally used.

The efficacy of vibegron on nocturnal pollakiuria in OAB patients was evaluated in a twelve-week randomized, double-blind, placebo-controlled, parallel-group study.

Japanese OAB patients received either vibegron (50 mg/day or 100 mg/day) or a placebo for 12 weeks. Both 50 mg/day of vibegron and 100 mg/day of vibegron were orally administered in the form of a tablet once daily after breakfast. Table 1 shows the demographic characteristics of subjects. There was no difference among the dose groups in terms of subject background such as gender, age, and BMI.

The therapeutic effect of vibegron on nocturnal pollakiuria in OAB patients was evaluated based on an average frequency of urination at night, which was determined by using a urination diary to investigate the frequency of urination for three days prior to visits. In this context, nighttime is defined as the period of time between when one goes to bed to sleep and when one wakes up and gets out of bed. The evaluation results are shown in Table 2 and FIG. 1. Constrained longitudinal data analysis model (cLDA) was used for statistical analysis to estimate the least squares mean and the two-sided 95% confidence interval of each group. Furthermore, the cLDA method was used to estimate the least squares mean difference at evaluation times between the 50 mg or 100 mg vibegron groups and the placebo group and the two-sided 95% confidence intervals thereof, thereby testing the least squares mean difference compared with placebo.

Numerical values in Table 2 represent the average of the frequency of urination at night at baseline (before drug administration), the least squares mean of the amount of change from baseline in the average frequency of urination at night after 12 weeks of administration, the least squares mean of difference in the amount of change between the vibegron groups and the placebo group, and p-values. In this regard, when the amount of change is less than 0, the smaller value represents a greater therapeutic effect. Furthermore, a p-value less than 0.05 indicates that there is a significant difference between the vibegron groups and the placebo group. "Patients whose frequency of urination at night is not zero at baseline" are represented as a main subject population, and other "patients whose frequency of urination at night is one or more times at baseline" and "patients whose frequency of urination at night is two or more times at baseline" are represented as populations who have more prominent symptoms of nocturnal pollakiuria. FIG. 1 is a graph in which the numerical values represent the least squares mean (ΔLSmean) of the amount of change from baseline in the frequency of urination at night after 12 weeks of administration.

TABLE 1

| | | Vibegron 50 mg Number of subjects: 370 | Vibegron 100 mg Number of subjects: 368 | Placebo Number of subjects: 369 |
|---|---|---|---|---|
| Demographic Characteristics | | | | |
| Gender | Number of female subjects (%) | 334 (90.3) | 330 (89.7) | 333 (90.2) |
| | Number of male subjects (%) | 36 (9.7) | 38 (10.3) | 36 (9.8) |
| Age | Mean value ± standard deviation | 58.0 ± 11.8 | 58.7 ± 11.1 | 58.9 ± 11.8 |
| BMI (kg/cm$^2$) | Mean value ± standard deviation | 23.00 ± 4.00 | 23.15 ± 4.16 | 23.22 ± 3.96 |
| OAB Disease duration (months) | Mean value ± standard deviation | 58.3 ± 63.2 | 69.8 ± 75.2 | 58.2 ± 59.3 |

TABLE 2

The Amount of Change from Baseline in the Frequency of Urination at Night after 12 Weeks of Administration

| Subject population | Dose group | Number of subjects | Average at baseline | Amount of change Least squares mean (95% confidence interval) | Difference in amount of change (vibegron group − placebo group) Least squares mean (95% confidence interval) | p-value |
|---|---|---|---|---|---|---|
| Patients whose frequency of urination at night is not zero at baseline | Vibegron 50 mg | 312 | 1.37 | −0.58 (−0.65, −0.51) | −0.11 (−0.21, −0.02) | 0.0158 |
| | Vibegron 100 mg | 304 | 1.36 | −0.62 (−0.70, −0.55) | −0.16 (−0.25, −0.06) | 0.0012 |
| | Placebo | 313 | 1.41 | −0.47 (−0.54, −0.40) | | |
| Patients whose frequency of urination at night is one or more times at baseline | Vibegron 50 mg | 227 | 1.69 | −0.74 (−0.82, −0.65) | −0.16 (−0.28, −0.04) | 0.0073 |
| | Vibegron 100 mg | 218 | 1.69 | −0.78 (−0.87, −0.70) | −0.21 (−0.33, −0.09) | 0.0007 |
| | Placebo | 224 | 1.75 | −0.58 (−0.66, −0.49) | | |
| Patients whose frequency of urination at night is two or more times at baseline | Vibegron 50 mg | 80 | 2.45 | −1.00 (−1.17, −0.83) | −0.15 (−0.38, 0.08) | 0.2051 |
| | Vibegron 100 mg | 76 | 2.51 | −1.16 (−1.34, −0.99) | −0.31 (−0.55, −0.08) | 0.0093 |
| | Placebo | 80 | 2.60 | −0.85 (−1.02, −0.68) | | |

As can be seen from Table 2 and FIG. 1, the 50 mg vibegron group and the 100 mg vibegron group exhibited a significant therapeutic effect on nocturnal pollakiuria in the patients who urinated at night (whose frequency of urination at night was not zero at baseline) compared with the placebo group. Furthermore, the vibegron groups also exhibited an excellent therapeutic effect on nocturnal pollakiuria in the populations having more prominent symptoms of nocturnal pollakiuria whose frequency of urination at night was one or more times or two or more times (one or more at baseline). It was found from the results described above that vibegron served as a highly effective therapeutic agent on nocturnal pollakiuria.

Figure 2:
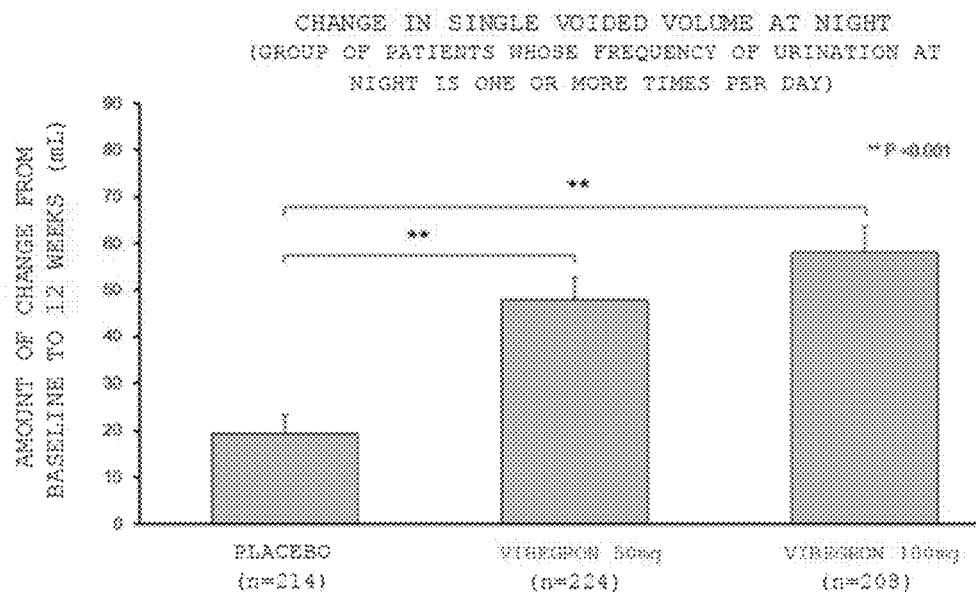
FIG. 2 is a graph showing the least squares mean (ΔLSmean) of the amount of change from baseline in the single voided volume at night after 12 weeks of administration in a group of patients whose frequency of urination at night is one or more times per day at baseline.

As is shown in FIG. 2, the single voided volume at night of the group of patients whose frequency of urination at night was one or more times per day (one or more at baseline) increased significantly in the 50 mg vibegron group (+47.85 mL) and the 100 mg vibegron group (+58.14 mL) compared with the placebo group (+19.42 mL). This result suggests that increase in the single voided volume at night possibly contributed to reduction in the frequency of urination at night.

Figure 3:
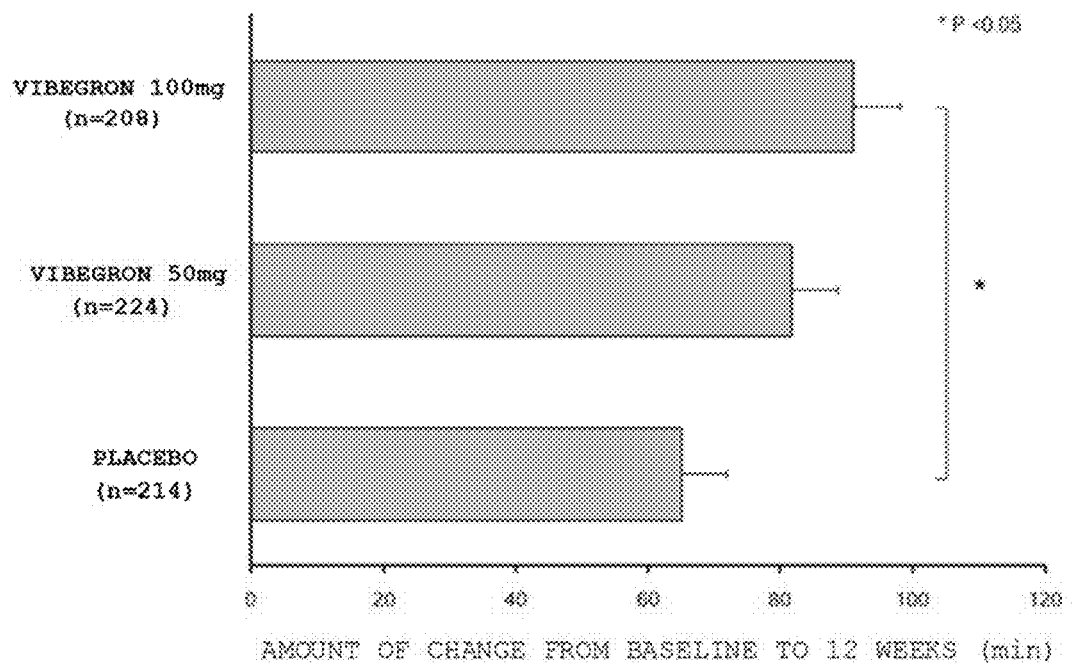
FIG. 3 is a graph showing the least squares mean (ΔLSmean) of the amount of change from baseline in the time to first awakening (HUS: hours of undisturbed sleep) after 12 weeks of administration in a group of patients whose frequency of urination at night is one or more times per day at baseline.
Figure 4:
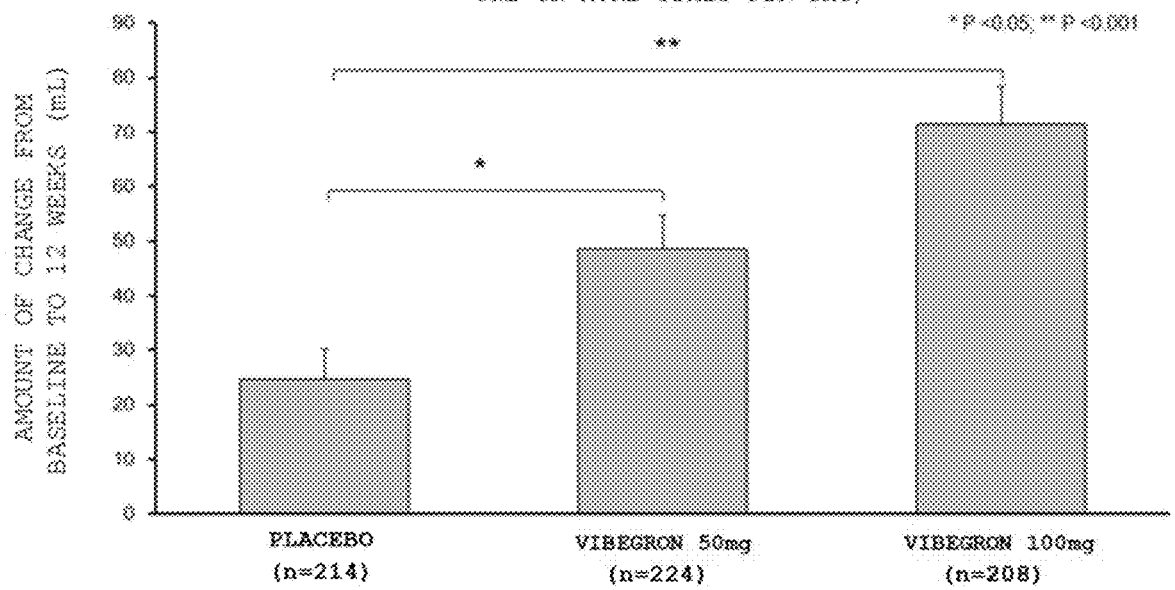
FIG. 4 is a graph showing the least squares mean (ΔLSmean) of the amount of change from baseline in the first voided volume at night after 12 weeks of administration in a group of patients whose frequency of urination at night is one or more times per day at baseline.

Furthermore, as is shown in FIG. 3, the time to first awakening of the group of patients whose frequency of urination at night was one or more times per day (one or more at baseline) was extended in the 50 mg vibegron group (81.79 minutes) and more significantly in the 100 mg vibegron group (90.95 minutes) compared with the placebo group (65.08 minutes). Furthermore, as is shown in FIG. 4, the first voided volume at night of the group of patients whose frequency of urination at night was one or more times per day (one or more at baseline) was increased significantly in the 50 mg vibegron group (48.71 mL) and the 100 mg vibegron group (71.42 mL) compared with the placebo group (24.80 mL).

TABLE 3

| Parameters | Vibegron 50 mg | | | Vibegron 100 mg | | |
|---|---|---|---|---|---|---|
| | n | p† | p-value | N | p† | p-value |
| (1) Time to first awakening vs. frequency of urination at night | 224 | −0.670 | <0.001 | 208 | −0.622 | <0.001 |
| (2) Time to first awakening vs. first voided volume at night | 224 | 0.419 | <0.001 | 208 | 0.423 | <0.001 |

†Spearman's rank correlation coefficient

It is found from Table 3 that there is positive correlation between the time to first awakening and the first voided volume at night (50 mg vibegron group: ρ=0.419, 100 mg vibegron group: ρ=0.423). It is also found that there is negative correlation between the time to first awakening and the frequency of urination at night (50 mg vibegron group: ρ=−0.670, 100 mg vibegron group: ρ=−0.622). The time to first awakening has been reported to be important for ensuring quality of sleep (Eur. Urol. Suppl. 2006; 5: 3-11), and moreover, it has been suggested that the first three hours of sleep contribute to quality of sleep (Sleep 1991; 14: 294-306). As described above, nocturnal pollakiuria greatly affects sleep and reduces QOL of patients. Considering this, vibegron is also promising as an agent for treating sleep disorders resulting from urination at night, since vibegron increases time to first awakening by reducing the frequency of urination at night as well as increasing the first voided volume at night.

The groups of patients whose frequency of urination at night was one or more times per day at baseline were compared based on the presence or absence of nocturnal polyuria.

In the group of patients with nocturnal pollakiuria without nocturnal polyuria, the frequency of urination at night was significantly reduced in the 50 mg vibegron group and the 100 mg vibegron group compared with the placebo group; and the single voided volume at night was significantly increased in the 50 mg vibegron group and the 100 mg vibegron group compared with the placebo group. On the other hand, in a group of patients with nocturnal pollakiuria with nocturnal polyuria, the frequency of urination at night was reduced in the 50 mg vibegron group and the 100 mg vibegron group compared with the placebo group but the difference was not significant. However, the single voided volume at night was significantly increased in the 50 mg vibegron group and the 100 mg vibegron group compared with the placebo group.

Desmopressin, which is an agonist of vasopressin V2 receptor, has been known so far as a drug for treating nocturnal pollakiuria: however, desmopressin has a risk of serious adverse reactions such as water intoxication (hyponatremia) and can be administered only to a restricted group of patients (Neurourol Urodyn 2004; 23: 302-305, Package inserts of Minirinmelt OD tablet 60 μg, Minirinmelt OD tablet 120 μg, and Minirinmelt OD tablet 240 μg, revised in March 2017 (the fourth edition)). In contrast, vibegron can be administered to more patients with nocturnal pollakiuria, since it is a highly safe compound, and thus, vibegron is an excellent agent for treating nocturnal pollakiuria.

INDUSTRIAL APPLICABILITY

This embodiment can provide a novel agent for treating nocturnal pollakiuria comprising (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide and is industrially useful.

The invention claimed is:

1. A method for treating nocturnal pollakiuria, comprising administering to a subject in need thereof (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide in an effective amount to treat nocturnal pollakiuria,
wherein the effective amount of the (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered to a subject belonging to a group of patients with nocturnal pollakiuria without nocturnal polyuria.

2. The method according to claim 1, wherein the effective amount of the (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered to a subject belonging to a group of patients whose average value of the frequency of urination at night is 1.0 or more and 1.8 or less.

3. The method according to claim 1, wherein the effective amount of the (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered orally once daily at a daily dosage of 50 mg or more and 100 mg or less.

4. The method according to claim 2, wherein the effective amount of the (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-a]pyrimidine-6-carboxamide is administered orally once daily at a daily dosage of 50 mg or more and 100 mg or less.

* * * * *